(12) United States Patent
Gritzky et al.

(10) Patent No.: US 10,157,500 B2
(45) Date of Patent: *Dec. 18, 2018

(54) UTILIZING DEPTH FROM ULTRASOUND VOLUME RENDERING FOR 3D PRINTING

(71) Applicant: General Electric Company, Schenectady, NY (US)

(72) Inventors: Arthur Gritzky, Oberösterreich (AT); Gerald Schroecker, Oberösterreich (AT)

(73) Assignee: General Electric Company, Schenectady, NY (US)

(*) Notice: Subject to any disclaimer, the term of this patent is extended or adjusted under 35 U.S.C. 154(b) by 184 days.

This patent is subject to a terminal disclaimer.

(21) Appl. No.: 14/984,340

(22) Filed: Dec. 30, 2015

(65) Prior Publication Data
US 2017/0109925 A1    Apr. 20, 2017

Related U.S. Application Data

(63) Continuation-in-part of application No. 14/882,979, filed on Oct. 14, 2015.

(51) Int. Cl.
*G06K 9/00*    (2006.01)
*G06T 17/20*    (2006.01)
(Continued)

(52) U.S. Cl.
CPC .......... *G06T 17/20* (2013.01); *A61B 8/466* (2013.01); *A61B 8/483* (2013.01); *G06T 15/08* (2013.01);
(Continued)

(58) Field of Classification Search
CPC ......... G06T 17/20; G06T 19/20; G06T 17/10; G06T 2210/41; G06T 7/0075;
(Continued)

(56) References Cited

U.S. PATENT DOCUMENTS 8,646,229 B2 * 2/2014 Grunewald ............... E04B 2/96
52/235
2009/0316966 A1 * 12/2009 Marshall ............... A61B 6/5217
382/128

(Continued)

OTHER PUBLICATIONS

Office Action in U.S. Appl. No. 14/882,979, dated Feb. 8, 2018. (11 pages).

(Continued)

*Primary Examiner* — Amir Alavi

(57) ABSTRACT

Systems and methods are provided for utilizing depth from volume rendering for 3D printing. Three-dimensional (3D) mesh data may be generated based on one or more volume rendered images and/or volumetric datasets corresponding thereto, obtained during medical imaging (e.g., based on echo ultrasound signals during ultrasound imaging). Generating the 3D mesh data may comprise computing a plurality of depth values, where each depth value corresponds to a particular voxel in the volumetric medical imaging datasets. The 3D mesh data may be configured to enable producing a physical volume representation of one or more objects and/or structures in the one or more volume rendered images. Thus, the 3D mesh data may be used for 3D printing. For example, 3D printing data may be generated based on the 3D mesh data. The 3D printing data may be configured and formatted based on a pre-defined 3D printing standard or file format.

20 Claims, 7 Drawing Sheets

(51) Int. Cl.
*G06T 15/08* (2011.01)
*A61B 8/00* (2006.01)
*B33Y 50/02* (2015.01)
*A61B 8/08* (2006.01)
*B33Y 50/00* (2015.01)
*B29C 64/386* (2017.01)

(52) U.S. Cl.
CPC ........... *A61B 8/0866* (2013.01); *B29C 64/386* (2017.08); *B33Y 50/00* (2014.12); *B33Y 50/02* (2014.12); *G06T 2210/41* (2013.01)

(58) Field of Classification Search
CPC ......... G06T 7/0022; G06T 2207/10012; G06T 15/08; A61B 8/14; B29C 67/0088; B33Y 50/02; H04N 13/0239; H04N 13/0082

See application file for complete search history.

(56) References Cited

U.S. PATENT DOCUMENTS

| | | | |
|---|---|---|---|
| 2014/0330418 A1 | 11/2014 | Wu | |
| 2015/0045662 A1* | 2/2015 | Kim | A61B 8/0883 |
| | | | 600/427 |
| 2015/0228070 A1* | 8/2015 | Birkbeck | G06T 7/0012 |
| | | | 382/131 |
| 2017/0085867 A1* | 3/2017 | Baran | H04N 13/0447 |
| 2017/0109925 A1* | 4/2017 | Gritzky | G06T 17/20 |
| 2017/0347120 A1* | 11/2017 | Chou | H04N 19/597 |
| 2017/0357406 A1* | 12/2017 | Yi | G06F 3/04815 |

OTHER PUBLICATIONS

Scott J Grunewald; "3D Printing Helps Expectant Patents Meet their Baby Before it's Born", Aug. 5, 2015. http://3dprint.com/87252/baby-boo-3d-print-fetus; 11 pages.
Mark Wilson; "It is Now Possible to 3D Print Your Unborn Fetus", Jan. 17, 2014. https://www.fastcodesign.com/3024940/it-is-now-possible-to-3-d-print-your-unborn-fetus; 16 pages.

* cited by examiner

UTILIZING DEPTH FROM ULTRASOUND VOLUME RENDERING FOR 3D PRINTING

CLAIMS OF PRIORITY

This application is a continuation-in-part (OP) of U.S. patent application Ser. No. 14/882,979 filed Oct. 14, 2015. The above identified application is hereby incorporated herein by reference in its entirety.

FIELD

Certain embodiments relate to medical imaging. More specifically, certain embodiments relate to methods and systems for utilizing depth from volume rendering for three-dimensional (3D) printing.

BACKGROUND

Various medical imaging techniques may be used, such as in imaging organs and soft tissues in a human body. Examples of medical imaging techniques include ultrasound imaging, computed tomography (CT) scans, magnetic resonance imaging (MRI), etc. The manner by which images are generated during medical imaging depends on the particular technique. For example, ultrasound imaging uses real time, non-invasive high frequency sound waves to produce ultrasound images, typically of organs, tissues, objects (e.g., fetus) inside the human body. Images produced or generated during medical imaging may be two-dimensional (2D), three-dimensional (3D), and/or four-dimensional (4D) images (essentially real-time/continuous 3D images).

Typically during medical imaging, imaging datasets (volumetric imaging datasets during 3D/4D imaging) are acquired and used in generating and rendering the corresponding images (e.g., via a display) in real-time. In some instances, however, it may be desirable to print copies of the images. For example, parents may want printouts of ultrasound images displayed during obstetric (OB) ultrasound imaging. Conventionally, only 2D printing (e.g. on flat sheets) is available, regardless of whether the images were 2D or 3D/4D.

Further limitations and disadvantages of conventional and traditional approaches will become apparent to one of skill in the art, through comparison of such systems with some aspects as set forth in the remainder of the present application with reference to the drawings.

BRIEF SUMMARY

A system and/or method is provided for utilizing depth from volume rendering for 3D printing, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION

Figure 1A:
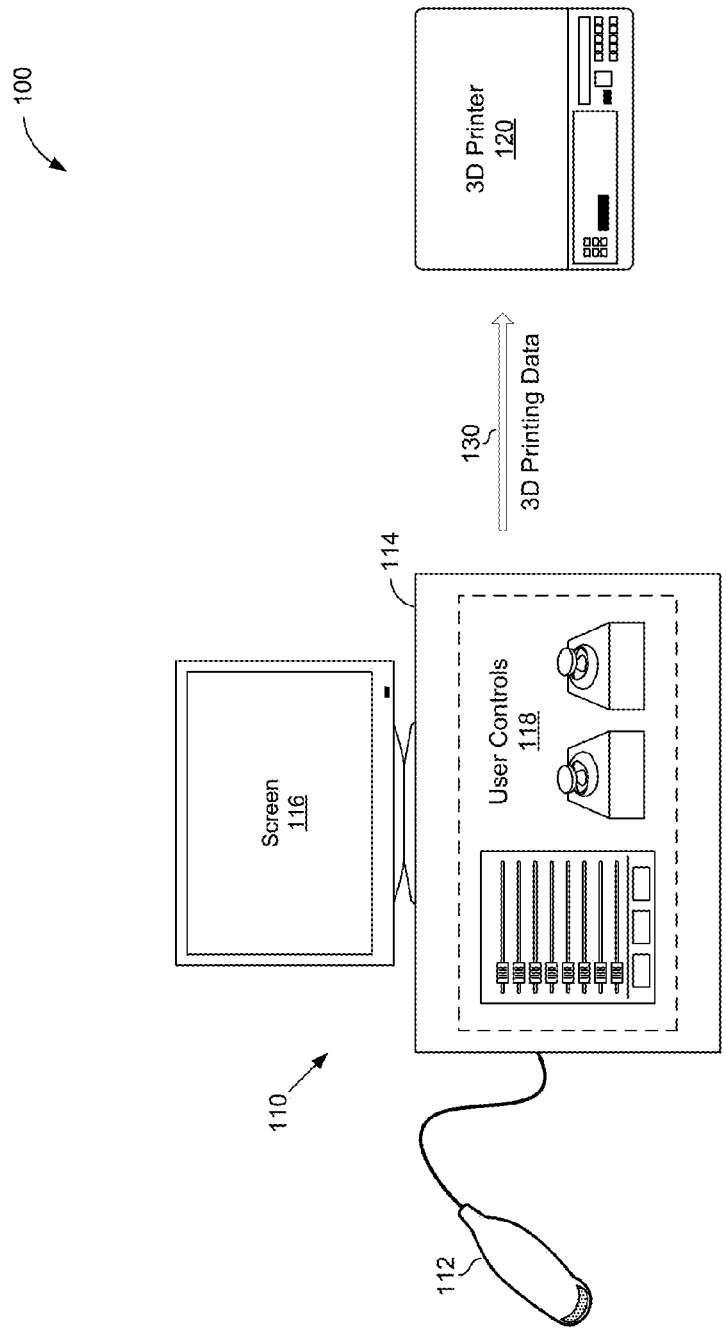
FIG. 1A is a block diagram illustrating an example medical imaging arrangement that supports three-dimensional (3D) printing, in accordance with an example embodiment.

Certain embodiments may be found in methods and systems for utilizing depth from volume rendering for three-dimensional (3D) printing. For example, aspects have the technical effect of facilitating 3D printing during medical (e.g., ultrasound) imaging by generating 3D mesh data based on the volume rendered images. In this regard, during medical imaging, volumetric datasets may be generated (e.g., based on echo ultrasound signals in ultrasound imaging), and volume rendered images may be generated and/or displayed, based on the volumetric datasets. The 3D mesh data may then be generated, based on the volume rendered images and/or the volumetric datasets, with the 3D mesh data being configured to enable producing a physical volume representation of one or more objects and/or structures in the volume rendered images. In particular, generating the 3D mesh data comprises computing a plurality of depth values, where each depth value corresponds to a particular voxel in the volumetric medical imaging datasets. The 3D mesh data may then be used for 3D printing. For example, the 3D mesh data may be used in generating 3D printing data, for enabling the 3D printing via a corresponding 3D printer. The 3D printing data may be configured and formatted based on a pre-defined 3D printing standard or file format supported by the 3D printer.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an example embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

In addition, as used herein, the phrase "pixel" also includes embodiments where the data is represented by a "voxel." Thus, both the terms "pixel" and "voxel" may be used interchangeably throughout this document.

Also as used herein, the term "image" broadly refers to both viewable images and data representing a viewable image. However, many embodiments generate (or are configured to generate) at least one viewable image. Further, with respect to ultrasound imaging, as used herein the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations, such as single or multi-core: CPU, Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams." Also, forming of images may be performed using channel combinations that may originate from more than one transmit event (e.g., synthetic aperture techniques).

In various embodiments, imaging processing, including visualization enhancement, to form images may be performed, for example, in software, firmware, hardware, or a combination thereof.

FIG. 1A is a block diagram illustrating an example medical imaging arrangement that supports three-dimensional (3D) printing, in accordance with an example embodiment. Shown in FIG. 1A is a setup 100, comprising a medical imaging system 110 and a 3D printer 120.

The medical imaging system 110 comprise suitable hardware, software, or a combination thereof, for supporting medical imaging—that is enabling obtaining data used in generating and/or rendering images during medical imaging exams. This may entail capturing of particular type of data, in particular manner, which may in turn be used in generating the data of the images. For example, the medical imaging system 110 may be an ultrasound system, configured for generating and/or rendering ultrasound images. An example implementation of an ultrasound system that may correspond to the medical imaging system 110 is described in more detail with respect to FIG. 2.

As shown in FIG. 1A, the medical imaging system 110 may comprise a probe 112, which may be portable and movable, and a display/control unit 114. The probe 112 may be used in generating and/or capturing particular type of signals (or data corresponding thereto), such as by being moved over a patient's body (or part thereof). For example, where the medical imaging system 110 is an ultrasound system, the probe 112 may emit ultrasound signals and capture echo ultrasound images.

The display/control unit 114 may be used in displaying images (e.g., via a screen 116). Further, the display/control unit 114 may support user interactions (e.g., via user controls 118), such as to allow controlling of the medical imaging. The user interactions may comprise user input or commands controlling display of images, selecting settings, specifying user preferences, providing feedback as to quality of imaging, etc.

The 3D printer 120 may be operable to perform 3D printing. In this regard, the 3D printer 120 may be configured to produce (e.g., synthesize) three-dimensional physical representations, such as based on the 3D printing data corresponding to and/or based on 3D model of the would-be printed objects. The 3D printer 120 may be any of commercially available products, which may be communicatively coupled to the medical imaging system 110, via suitable connections, wired (e.g., cords) and/or wireless (e.g., WiFi, Bluetooth, etc.). The 3D printer 120 may also be part of the medical imaging system 110 itself, and may even by incorporated directly into it.

In operation, the medical imaging system 110 may be used in generating and presenting (e.g., rendering or displaying) images, and/or in supporting user input in conjunction therewith. The images may be 2D, 3D, and/or 4D images. The particular operations or functions performed in the medical imaging system 110 to facilitate the generating and/or presenting of images depends on the type of system—that is the manner by which the data corresponding to the images is obtained and/or generated. For example, in ultrasound imaging, the data is based on emitted and echo ultrasound signals, as described in more detail with respect to FIG. 2.

The medical imaging system 110 may be operable to support three-dimensional (3D) printing (e.g., via the 3D printer 120). Typically copies of images rendered during medical imaging (e.g., ultrasound scans) are only are only printed two-dimensionally (e.g., as 2D black-and-white or colored sheets) regardless of whether the images were rendered as 2D images or volumetric images (e.g., 3D/4D). As noted above, it may be desirable provide three-dimensional (3D) printing, however. In this regard, 3D printing may comprise generating physical volume (e.g., 3D) representations of objects and/or structures in displayed images. For example, expecting parent(s) may want to have 3D printouts of the ultrasound images displayed during obstetric (OB) imaging scans (e.g., the fetus and/or particular features thereof, such as the face), as a keepsake. The 3D printouts (or data corresponding thereto) may also be useful as reference for medical services (e.g., to help generate a model for use in surgical planning, etc.) both close to the time of the medical imaging and in the future.

For example, three-dimensional (volume) physical objects may be synthesized, using suitable 3D printers (e.g., the 3D printer 120). Such 3D printers may utilize, for example, additive processes to lay successive layers of material. The synthesized volume objects may be of almost any shape and/or geometry. The 3D printers and/or operations thereof (during 3D printing) may be configured and/or controlled based on data (referred to hereafter as "3D printing data.") The 3D printing data may comprise information corresponding to and/or representing the would-be printed objects (or structures thereof). The 3D printing data may be generated and/or formatted in accordance with one or more defined formats for use in 3D printing, such as STL (STereoLithography) file format based data. Further, in some instances, the 3D printing data may comprise and/or be based on 3D modeling (or information relating thereto) of the would-be printed objects.

With respect to medical imaging, information obtained and/or generated to enable volumetric images or rendering thereof may be used in facilitating 3D printing. For example, the 3D printing data may be done by using volumetric datasets acquired and/or generated during medical imaging to generate the 3D printing data and/or the 3D modeling of the would-be printed objects. For example, in the medical imaging system 110 during 3D/4D imaging volumetric datasets may be generated and/or acquired to facilitate the 3D/4D rendering. Such volumetric datasets may be used in generating and/or configuring 3D printing data 130, which may be provided (e.g., communicated, such as via wired and/or wireless connections) to the 3D printer 120. In this regard, the 3D printing data 130 may be generated and/or configured based on 3D modeling of the objects and/or structures in the images, and may be formatted based on the supported printing data formats in the 3D printer 120.

Figure 1B:
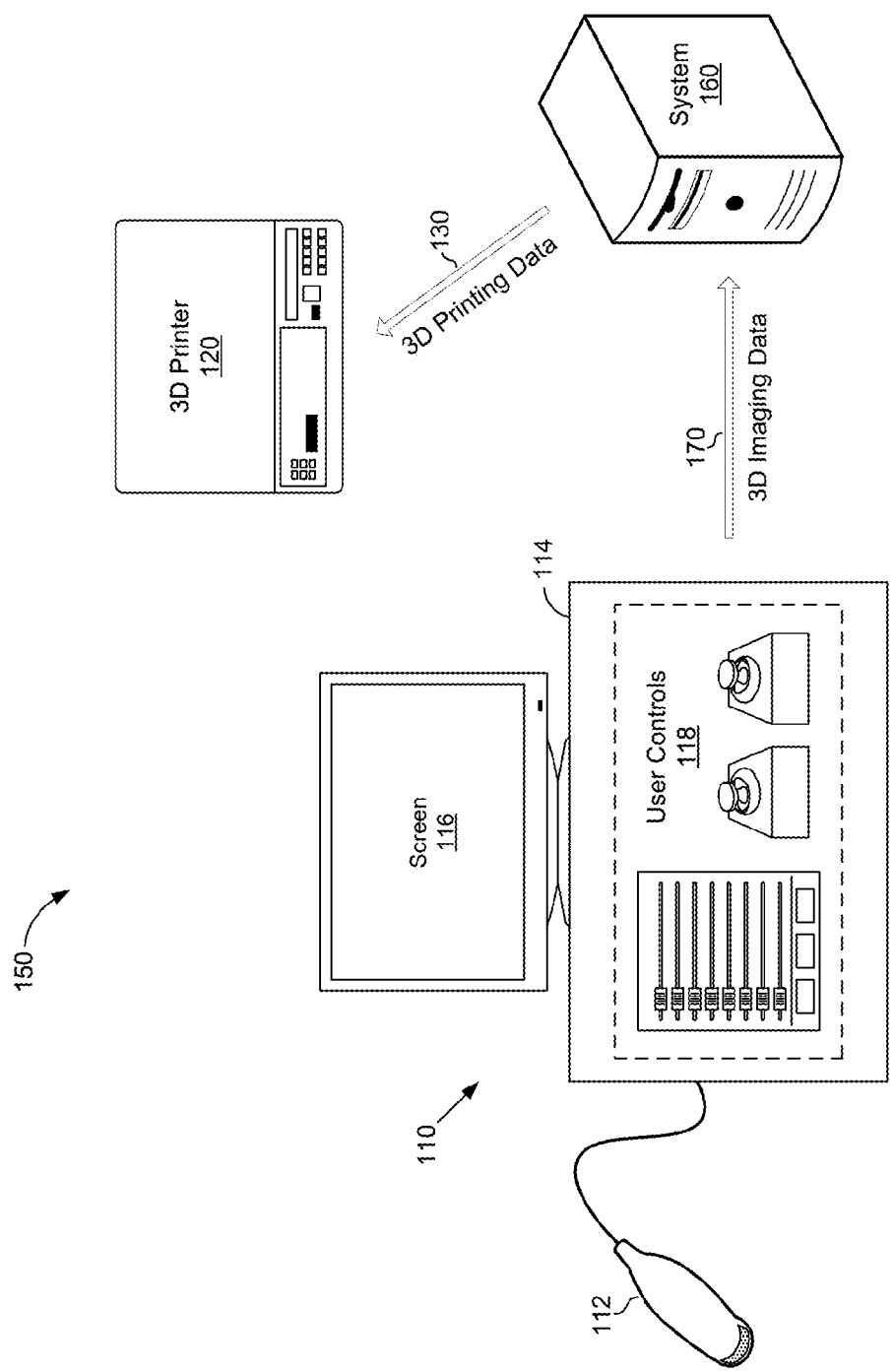
FIG. 1B is a block diagram illustrating an example medical imaging arrangement that supports three-dimensional (3D) printing, with offloaded 3D print data processing, in accordance with an example embodiment.

As illustrated in FIG. 1A, the generation of the 3D printing data 130 is shown as being done directly in the medical imaging system 110 (e.g., within the display/control unit 114, using suitable processing circuitry therein). The disclosure is not so limited, however. Rather, in some instances, at least some of the processing performed to generate the 3D printing data based on the imaging related information may be offloaded to a dedicated system, which may be located near or remote from the imaging setup. An example of such arrangement is shown in FIG. 3B, which is a block diagram illustrating an example medical imaging arrangement that supports three-dimensional (3D) printing, with offloaded 3D print data processing, in accordance with an example embodiment. Shown in FIG. 1B is a setup 150 comprising the medical imaging system 110 and the 3D printer 120 as well as a computing system 160.

The computing system 160 may comprise suitable circuitry for processing, storing, and/or communication data. In this regard, the computing system 160 may be operable to receive 3D imaging data 170 (which may comprise volumetric imaging datasets, information relating thereto that may be used, e.g., in 3D modeling, and/or 3D modeling related information generated in the medical imaging system 110); to process the received 3D imaging data 170, to generate the 3D printing data 130; and to transmit the 3D printing data 130 to the 3D printer 120. The computing system 160 may be a dedicated equipment configured particularly for use in conjunction with medical imaging, including in support of 3D printing; or it may be a general purpose computing system (e.g., personal computer, server, etc.) setup and/or configured to perform the operations described with respect to the computing system 160. Communications between the different elements in the setup 150 may be done using available wired and/or wireless connections, and/or in accordance any suitable communication (and/or networking) standards or protocols.

In an example implementation, the 3D printing data 130 may be generated (e.g., via the via the medical imaging system 110 or the computing system 160) based on surface mesh representation, such as a 2D or 3D polygon (e.g., triangle) mesh, which may be generated based on the volumetric datasets acquired via the medical imaging system 110 and/or volume rendering based thereon. In an example use scenario, a direct volume rendering may be used in generating 2D image from a volumetric dataset. For example, in instances where imaging is configured based on the RGB color model (to provide colored images), in addition to the RGB color information forming the 2D image, a depth value is computed for every pixel. The depth information may then be used in creating a relief-like mesh (e.g., polygon mesh), where the depth values are used as the height for a regular grid of vertices which are connect by polygons (e.g., triangles) to form a closed mesh. The depth value may be the centroid of the opacity increase for each ray along depth. An example of generation of a mesh representation based on volume datasets and/or volume rendering during medical (e.g., ultrasound) imaging is illustrated in more detail with respect to FIGS. 3A-3C, below.

Providing 3D printing in this manner—that is based on and/or in conjunction with medical imaging—is advantageous. This approach would ensure that 3D prints (objects) would look exactly as the rendering on the screen 116. Also, a fully automated workflow from volume data to 3D printing is possible with this approach, allowing for efficient and/or easy-to-use operation. Further, the rendering operations may enhance the quality of the 3D printing—e.g., the rendering algorithm may act as non-linear filter smoothing the data and producing very reliable depth information compared to other segmentation methods. The rendered image (which matches the mesh) may also be used in texturing (e.g., colorizing) the 3D prints, the enhance quality (e.g., realism) of printed objects. This approach may also allow for control of the 3D printing by the user, such as based on user input (provided via the user controls 118). For example, the 3D printing may be controlled by the user based on user input relating to the volume rendering (e.g., selection of viewpoint, scaling, threshold, etc.). Further, the 3D printing may reflect use of techniques available for volume rendering, such as to cut away unwanted parts of the volume (e.g., masking with MagiCut, Vocal, Threshold, etc.). In other words, the 3D prints may only include the wanted parts of the objects.

Additional details are provided below, in FIGS. 2 and 3A-3C, regarding 3D printing functions and/or operations, including generation of 3D printing, based on volumetric datasets obtained and/or generated respect to FIG. 2, as well as various considerations and/or techniques. These figures are described in the context of ultrasound imaging, particularly in conjunction with generation of 3D printing data in such scenarios. It should be understood, however, that the disclosure is not so limited, and these described embodiments are only example implementations that may be applied in substantially similar manner to other forms of medical imaging.

Figure 2:
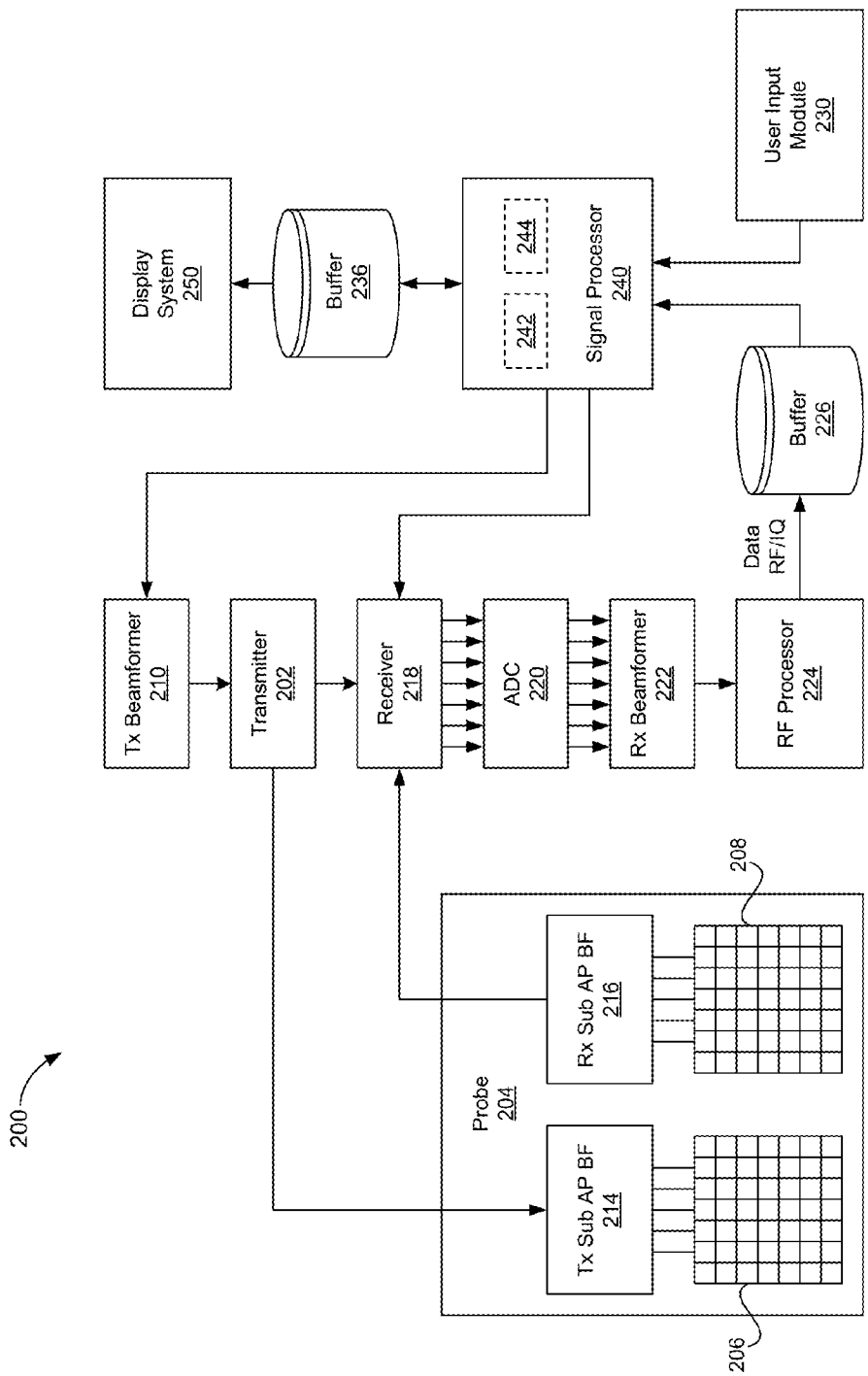
FIG. 2 is a block diagram illustrating an example ultrasound system that may be used in ultrasound imaging, which may support three-dimensional (3D) printing, in accordance with various embodiments.

FIG. 2 is a block diagram illustrating an example ultrasound system that may be used in ultrasound imaging, which may support three-dimensional (3D) printing, in accordance with various embodiments. Shown in FIG. 2 is an ultrasound system 200.

The ultrasound system 200 may comprise suitable components (physical devices, circuitry, etc.) for providing ultrasound imaging. The ultrasound system 200 may correspond to the medical imaging system 110 of FIG. 1 in ultrasound imaging use scenarios. The ultrasound system 200 comprises, for example, a transmitter 202, an ultrasound probe 204, a transmit beamformer 210, a receiver 218, a receive beamformer 222, a RF processor 224, a RF/IQ buffer 226, a user input module 230, a signal processor 240, an image buffer 236, and a display system 250.

The transmitter 202 may comprise suitable circuitry that may be operable to drive an ultrasound probe 204. The transmitter 202 and the ultrasound probe 204 may be implemented and/or configured for one-dimensional (1D), two-dimensional (2D), three-dimensional (3D), and/or four-dimensional (4D) ultrasound scanning. The ultrasound probe 204 may comprise a one-dimensional (1D, 2.25D, 2.5D or 2.75D) array or a two-dimensional (2D) array of piezoelectric elements. For example, as shown in FIG. 2, the ultrasound probe 204 may comprise a group of transmit transducer elements 206 and a group of receive transducer elements 208, that normally constitute the same elements. The transmitter 202 may be driven by the transmit beamformer 210.

The transmit beamformer 210 may comprise suitable circuitry that may be operable to control the transmitter 202 which, through a transmit sub-aperture beamformer 214, drives the group of transmit transducer elements 206 to emit ultrasonic transmit signals into a region of interest (e.g., human, animal, underground cavity, physical structure and the like). In this regard, the group of transmit transducer elements 206 can be activated to transmit ultrasonic signals. The ultrasonic signals may comprise, for example, pulse sequences that are fired repeatedly at a pulse repetition frequency (PRF), which may typically be in the kilohertz range. The pulse sequences may be focused at the same transmit focal position with the same transmit characteristics. A series of transmit firings focused at the same transmit focal position may be referred to as a "packet."

The transmitted ultrasonic signals may be back-scattered from structures in the object of interest, like tissue, to produce echoes. The echoes are received by the receive transducer elements 208. The group of receive transducer elements 208 in the ultrasound probe 204 may be operable to convert the received echoes into analog signals, undergo sub-aperture beamforming by a receive sub-aperture beamformer 216 and are then communicated to the receiver 218.

The receiver 218 may comprise suitable circuitry that may be operable to receive and demodulate the signals from the probe transducer elements or receive sub-aperture beamformer 216. The demodulated analog signals may be communicated to one or more of the plurality of A/D converters (ADCs) 220.

Each plurality of A/D converters 220 may comprise suitable circuitry that may be operable to convert analog signals to corresponding digital signals. In this regard, the plurality of A/D converters 220 may be configured to convert demodulated analog signals from the receiver 218 to corresponding digital signals. The plurality of A/D converters 220 are disposed between the receiver 218 and the receive beamformer 222. Notwithstanding, the disclosure is not limited in this regard. Accordingly, in some embodiments, the plurality of A/D converters 220 may be integrated within the receiver 218.

The receive beamformer 222 may comprise suitable circuitry that may be operable to perform digital beamforming processing to, for example, sum the delayed channel signals received from the plurality of A/D converters 220 and output a beam summed signal. The resulting processed information may be converted back to corresponding RF signals. The corresponding output RF signals that are output from the receive beamformer 222 may be communicated to the RF processor 224. In accordance with some embodiments, the receiver 218, the plurality of A/D converters 220, and the beamformer 222 may be integrated into a single beamformer, which may be digital.

The RF processor 224 may comprise suitable circuitry that may be operable to demodulate the RF signals. In some instances, the RF processor 224 may comprise a complex demodulator (not shown) that is operable to demodulate the RF signals to form In-phase and quadrature (IQ) data pairs (e.g., B-mode data pairs) which may be representative of the corresponding echo signals. The RF (or IQ) signal data may then be communicated to an RF/IQ buffer 226.

The RF/IQ buffer 226 may comprise suitable circuitry that may be operable to provide temporary storage of output of the RF processor 224—e.g., the RF (or IQ) signal data, which is generated by the RF processor 224.

The user input module 230 may comprise suitable circuitry that may be operable to enable obtaining or providing input to the ultrasound system 200, for use in operations thereof. For example, the user input module 230 may be used to input patient data, surgical instrument data, scan parameters, settings, configuration parameters, change scan mode, and the like. In an example embodiment, the user input module 230 may be operable to configure, manage and/or control operation of one or more components and/or modules in the ultrasound system 200. In this regard, the user input module 230 may be operable to configure, manage and/or control operation of transmitter 202, the ultrasound probe 204, the transmit beamformer 210, the receiver 218, the receive beamformer 222, the RF processor 224, the RF/IQ buffer 226, the user input module 230, the signal processor 240, the image buffer 236, and/or the display system 250.

The signal processor 240 may comprise suitable circuitry that may be operable to process the ultrasound scan data (e.g., the RF and/or IQ signal data) and/or to generate corresponding ultrasound images, such as for presentation on the display system 250. The signal processor 240 is operable to perform one or more processing operations according to a plurality of selectable ultrasound modalities on the acquired ultrasound scan data. In some instances, the signal processor 240 may be operable to perform compounding, motion tracking, and/or speckle tracking. Acquired ultrasound scan data may be processed in real-time—e.g., during a B-mode scanning session, as the B-mode echo signals are received. Additionally or alternatively, the ultrasound scan data may be stored temporarily in the RF/IQ buffer 226 during a scanning session and processed in less than real-time in a live or off-line operation.

In operation, the ultrasound system 200 may be used in generating ultrasonic images, including two-dimensional (2D), three-dimensional (3D), and/or four-dimensional (4D) images. In this regard, the ultrasound system 200 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 250 at a display-rate that can be the same as the frame rate, or slower or faster. An image buffer 236 is included for storing processed frames of acquired ultrasound scan data that are not scheduled to be displayed immediately. Preferably, the image buffer 236 is of sufficient capacity to store at least several seconds' worth of frames of ultrasound scan data. The frames of ultrasound scan data are stored in a manner to facilitate retrieval thereof according to its order or time of acquisition. The image buffer 236 may be embodied as any known data storage medium.

In some instances, the ultrasound system 200 may be configured to support grayscale and color based operations. For example, the signal processor 240 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data. The display data may be converted to X-Y format for video display. The scan-converted frames can be mapped to grayscale for display. The B-mode frames that are provided to the image buffer 236 and/or the display system 250. The color processing may comprise processing color based RF signal data or IQ data pairs to form frames to overlay on B-mode frames that are provided to the image buffer 236 and/or the display system 250. The grayscale and/or color processing may be adaptively adjusted based on user input—e.g., a selection from the user input module 230, for example, for enhance of grayscale and/or color of particular area.

In some instances, ultrasound imaging may include generation and/or display of volumetric ultrasound images— that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 240) to generate the corresponding volumetric datasets, which may in turn be used (e.g., via a 3D rendering module 242 in the signal processor 240) in creating and/or displaying volume (e.g. 3D) images, such as via the display 250. This may entail use of particular handling techniques to provide the desired 3D perception. For example, volume rendering techniques may be used in displaying projections (e.g., 2D projections) of the volumetric (e.g., 3D) datasets. In this regard, rendering a 2D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In some instances, ultrasound imaging may include generation and/or display of volumetric ultrasound images— that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 240) to generate the corresponding volumetric datasets, which may in turn be used (e.g., via a 3D rendering module 242 in the signal processor 240) in creating and/or displaying volume (e.g. 3D) images, such as via the display 250. This may entail use of particular handling techniques to provide the desired 3D perception.

For example, volume rendering techniques may be used in displaying projections (e.g., 2D projections) of the volumetric (e.g., 3D) datasets. In this regard, rendering a 2D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In some instances, the ultrasound system 200 may support 3D printing, substantially as described with regard to FIGS. 1A-1B. This may be done by, for example, utilizing volumetric ultrasound datasets (e.g., via a 3D printing module 244 in the signal processor 240 of the ultrasound system 200, or via an external system, such as the computing system 160, to which the volumetric ultrasound datasets may be communicated) to generate and/or configure 3D printing data, which may be provided to 3D printers to perform the 3D printing (e.g., the 3D printer 120 in the imaging setups depicted in FIGS. 1A-1B).

Some challenges may exist when generating such 3D printing data, however. For example, quality of the 3D printing may (e.g., due to quality and/or accuracy of the 3D printing data) depend on and/or be adversely affected by characteristics of the ultrasound imaging, such as bad signal quality (e.g., due to noise, speckle, acoustic shadowing, etc.), difficult tissue differentiation with no defined gray values to distinguish anatomical objects, etc. Thus, the generation of 3D printing data (e.g., via the 3D printing module 244) based on the ultrasound imaging and/or the volumetric ultrasound datasets acquired during such imaging may be configured and/or adjusted to optimize the quality of 3D printing, such as by adaptively configuring and/or controlling the generation of the 3D printing data, to account for such issues and/or defects for example.

In some example embodiments, the 3D printing data may be generated based on surface mesh representation (e.g., polygon mesh) suitable for 3D printing. A polygon mesh may be a collection of vertices, edges, and/or polygons faces (e.g., triangles, quadrilaterals, etc.) for defining the shape of an object in a polyhedral manner, to facilitate 3D modeling of that object. Such surface mesh representations may be obtained by, for example, converting 3D scalar volume data. For example, depth information may be extracted (e.g., via the 3D rendering module 242) based on volumetric ultrasound datasets and/or volume rendering, and this depth information may then be used in creating a relief like mesh.

Computation of depth values may be adaptively configured and/or applied based on the manner by which volume rendering is done. For example, with conventional rendering with opaque polygons, when an object is rendered, the depth of a generated pixel may be stored, such as in a dedicated depth buffer (e.g., a subsection of the image buffer 236). The depth buffer may be arranged as a two-dimensional array (x-y) with one element for each screen pixel. If another object of the scene must be rendered in the same pixel, the two depths are compared, and the current pixel is overridden if the object is closer to the observer. The chosen depth may be then saved to the depth buffer, replacing the old one. Once fully (or sufficiently) populated, the depth buffer may allow for correctly reproducing the usual depth perception—that is allowing a close object to hide a farther one.

With volume rendering there may be no polygons. Instead, volume ray casting algorithm may be used, to generate a depth map corresponding to the object or structure to be printed. This may be achieved with the following steps: 1) for each pixel of the final image, a ray of sight is cast through the volume, and 2) along the part of the ray that lies within the volume, equidistant sampling points or samples may be selected. Generally, the volume may not be aligned with the ray of sight, and sampling points will usually be located in between voxels. Because of that, it may be necessary to interpolate the values of the samples from its surrounding voxels. To that end the following transfer function may be used to map each sampling point to opacities and colors as needed for the α-compositing combining all the values along the ray, thus facilitating the generation of depth map:

$$Depth_{Out} = Depth_{In} + (1-\alpha_{In})\alpha_i \, Depth_i$$

$$\alpha_{Out} = \alpha_{In} + (1-\alpha_{In})\alpha_i$$

where $Depth_i$ and $\alpha_i$ are the values at the current sampling point (index i), and where $Depth_{In}$ and $\alpha_{In}$ are initialized to 0.

The mesh representation may then be generated based on the depth map. For example, an array of vertices which define the position in space and an array of indices which define how the individual vertices are connected to triangles may be generated, using the depth information (e.g., depth map). For the array of vertices, for the width of the depth map, vertices may be defined at each (x,y) position, using the corresponding value in the depth map for that point (x,y). The array of indices may be then constructed as 2-dimensional array configured and populated based on the width and height of the depth map.

The surface mesh representation may be a 2D mesh. In certain example embodiments, however, 3D mesh representations may be created. For example, two or more volume renderings, such as from different viewing directions, may be used to create not only a relief mesh but a full 3D mesh. An example use scenario for generating a mesh representation based on volume datasets and/or volume rendering during ultrasound imaging is shown with respect to FIGS. 3A-3C, below.

Figure 3A:
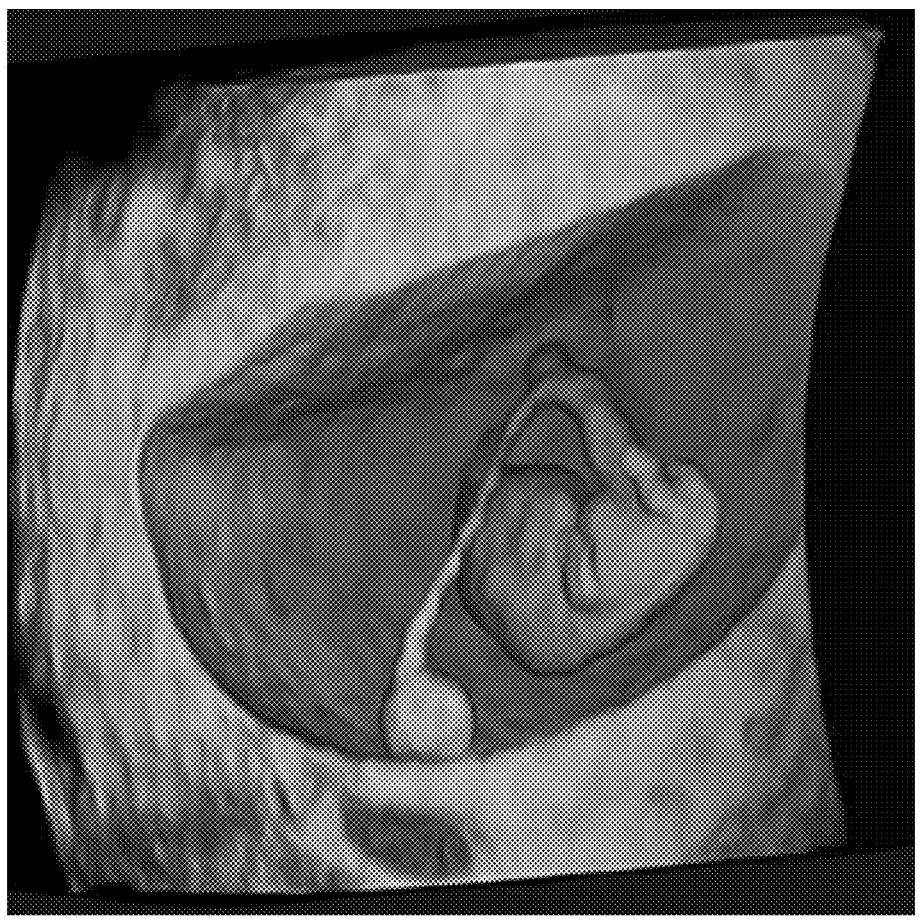
FIGS. 3A-3C illustrate example use of data corresponding to ultrasound volume rendering in generating polygon meshes for three-dimensional (3D) printing.
Figure 3B:
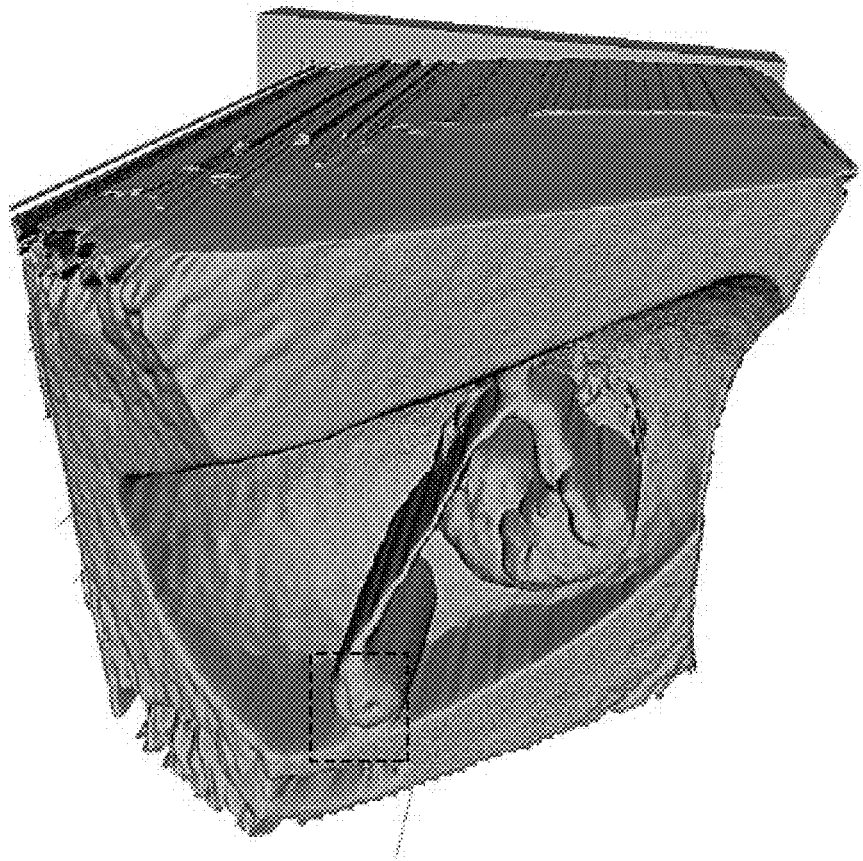
Figure 3C:

FIGS. 3A-3C illustrate example use of data corresponding to ultrasound volume rendering in generating polygon meshes for three-dimensional (3D) printing, in accordance with an example embodiment.

Shown in FIG. 3A is a volume rendered image 310, with depth. The image 310 may be rendered using volumetric ultrasound datasets, which may be acquired via an ultrasound system, such as the ultrasound system 200 of FIG. 2. The volumetric ultrasound datasets may comprise data (e.g., relating to ultrasound echoes) obtained from one or more angles or directions. Once acquired, the volumetric ultrasound datasets may be processed for volume (3D) rendering, such as via the 3D rendering module 242 of the signal processor 240. The volume rendering may comprise generating a projection (e.g., 2D projection) that provides the desired 3D perception. Processing relating to the volume rendering may comprise, for example, determining depth information (e.g., for each voxel), and using that depth information in the 2D projection.

Shown in FIG. 3B is an example mesh 320, which may be generated (e.g., from a slightly different angle) based on the volume rendered image 310 or volumetric dataset corresponding thereto, substantially as described above. In this regard, the mesh 320 may be created using depth values computed for the volume rendered image 310 (e.g., from the volumetric dataset, for every voxel), based on the defined angle for the mesh 320, such as by applying the depth values as the height for each regular grid of vertices which are connect by polygons (e.g., triangles) to form the mesh 310. Details of an example mesh are shown in FIG. 3C, which depicts a zoomed-in section 330 in the mesh 320 (shown as a dashed box in FIG. 3B) to illustrated polygons in the mesh.

Figure 4:
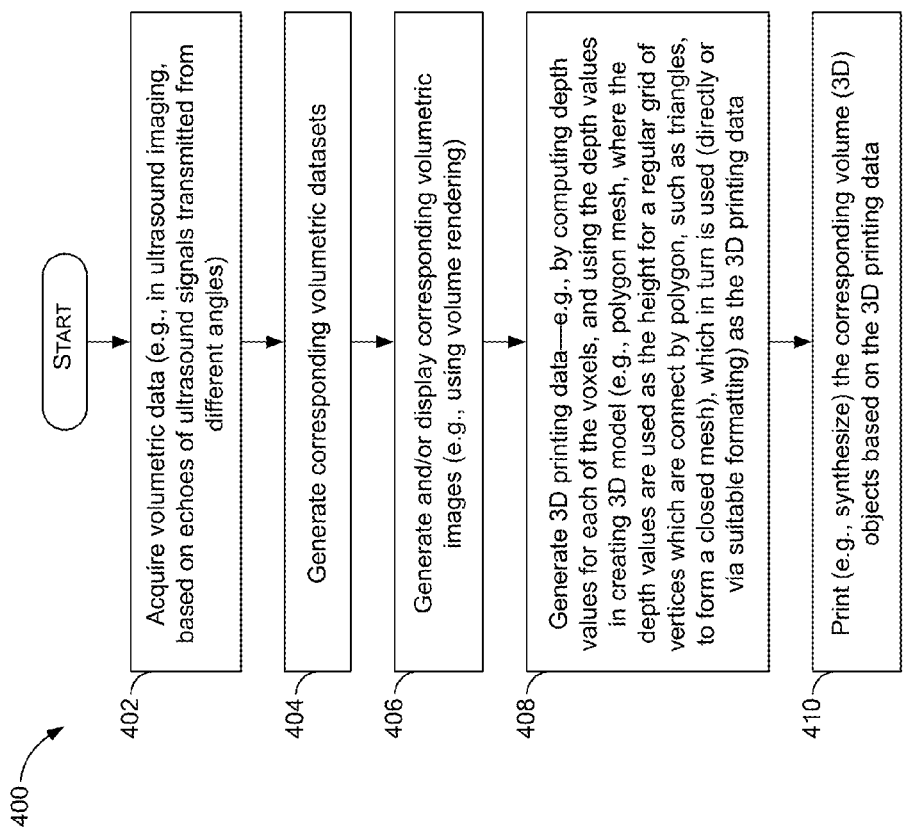
FIG. 4 is a flow chart illustrating example steps that may be performed for utilizing data from volume rendering for three-dimensional (3D) printing.

FIG. 4 is a flow chart illustrating example steps that may be performed for utilizing data from volume rendering for three-dimensional (3D) printing, in accordance with an embodiment. Shown in FIG. 4 is a flow chart 400, which comprises a plurality of example steps, corresponding to an example method.

The technical effect of the method corresponding to flow chart 400 is supporting three-dimensional (3D) printing (e.g., by generating data or files based thereon using the in 3D printers) based on the data acquired and/or generated for volume rendering in a medical imaging system or setup. For example, the example steps of the method corresponding to flow chart 400 may be executed and/or performed by the various components of the setups 100 or 150 of FIGS. 1A-1B, or the ultrasound system 200 of FIG. 2).

It should be understood, however, that certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

In step 402, after a start step (in which a medical imaging system may be, for example, initialized and/or configured for medical imaging), volumetric data may be acquired. For example, in ultrasound imaging, the volumetric data may be acquired based on echoes of ultrasound signal transmitted from different angles.

In step 404, corresponding volumetric datasets may be generated based on the acquired data.

In step 406, corresponding volumetric images may be generated and/or presented (e.g., using volume rendering).

In step 408, 3D printing data may be generated. This may be done (e.g., as described above with respect to FIG. 2) by computing depth values for each of the voxels, and using the depth values in creating 3D model (e.g., polygon mesh, where the depth values are used as the height for a regular grid of vertices which are connect by polygon, such as triangles, to form a closed mesh), which in turn may be used (directly or via suitable formatting) as the 3D printing data.

In step 410, the corresponding volume (3D) objects may be printed (e.g., synthesized) based on the 3D printing data.

As utilized herein the term "circuitry" refers to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or." As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "example" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for utilizing depth from volume rendering for three-dimensional (3D) printing.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A system, comprising:
   an electronic device comprising at least one processor, the electronic device is operable to:
   generate, based on at least one of one or more volume rendered images and volumetric medical imaging datasets corresponding to the one or more volume rendered images, three-dimensional (3D) mesh data;
   wherein:
   the 3D mesh data is configured to enable producing a physical volume representation of at least one of one or more objects and structures in the one or more volume rendered images; and
   generating the 3D mesh data comprises computing a plurality of depth values, where each depth value corresponds to a particular voxel in the volumetric medical imaging datasets.

2. The system of claim 1, wherein the 3D mesh data is used for 3D printing.

3. The system of claim 2, wherein the electronic device is operable to generate 3D printing data, based on the 3D mesh, to enable the 3D printing via a corresponding 3D printer.

4. The system of claim 3, wherein the electronic device is operable to configure and format the 3D printing data based on a pre-defined 3D printing standard or file format supported by the 3D printer.

5. The system of claim 1, wherein the electronic device is operable, when generating the 3D mesh data, to:
   compute one or more depth values corresponding to at least the portion of at least the one of the one or more volume rendered images; and
   apply the computed one or more depth values as height to a grid of plurality of vertices connected by a plurality of polygons.

6. The system of claim 1, wherein the electronic device is operable to:
   receive user input; and
   adaptively control generating the 3D mesh data in response to the user input.

7. The system of claim 1, wherein the electronic device is operable to receive the volumetric medical imaging datasets from a medical imaging device that is operable to generate based on a particular imaging technique.

8. The system of claim 1, wherein the electronic device comprises a medical imaging device operable to generate the volumetric medical imaging datasets based on a particular imaging technique.

9. A method, comprising:
   generating, based on at least one of one or more volume rendered images and volumetric medical imaging datasets corresponding to the one or more volume rendered images, three-dimensional (3D) mesh data;
   wherein:
   the 3D mesh data is configured to enable producing a physical volume representation of at least one of one or more objects and structures in the one or more volume rendered images; and
   generating the 3D mesh data comprises computing a plurality of depth values, where each depth value corresponds to a particular voxel in the volumetric medical imaging datasets.

10. The method of claim 9, wherein the 3D mesh data is used for 3D printing.

11. The method of claim 10, comprising generating 3D printing data, based on the 3D mesh data, to enable the 3D printing via a corresponding 3D printer.

12. The method of claim 11, comprising configuring and formatting the 3D printing data based on a pre-defined 3D printing standard or file format supported by the 3D printer.

13. The method of claim 9, comprising generating the 3D mesh data by:
   computing one or more depth values corresponding to at least the portion of at least the one of the one or more volume rendered images; and
   applying the computed one or more depth values as height to a grid of plurality of vertices connected by a plurality of polygons.

14. The method of claim 9, comprising:
   receiving user input; and
   adaptively controlling the generating of the 3D mesh data in response to the user input.

15. The method of claim 9, comprising generating the volumetric medical imaging datasets based on a particular imaging technique.

16. The method of claim 15, wherein the particular imaging technique comprises ultrasound imaging; and comprising:
   generating the volumetric medical imaging datasets based on captured echo ultrasound signals.

17. A non-transitory computer readable medium having stored thereon, a computer program having at least one code section, the at least one code section being executable by a machine for causing the machine to perform one or more steps comprising:

generating, based on at least one of one or more volume rendered images and volumetric medical imaging datasets corresponding to the one or more volume rendered images, three-dimensional (3D) mesh data;

wherein:

the 3D mesh data is configured to enable producing a physical volume representation of at least one of one or more objects and structures in the one or more volume rendered images; and generating the 3D mesh data comprises computing a plurality of depth values, where each depth value corresponds to a particular voxel in the volumetric medical imaging datasets.

18. The non-transitory computer readable medium of claim 17, comprising generating 3D printing data, based on the 3D mesh data, to enable 3D printing via a corresponding 3D printer.

19. The non-transitory computer readable medium of claim 18, comprising configuring and formatting the 3D printing data based on a pre-defined 3D printing standard or file format supported by the 3D printer.

20. The non-transitory computer readable medium of claim 17, comprising, when generating the 3D mesh data:

computing one or more depth values corresponding to at least the portion of at least the one of the one or more volume rendered images; and applying the computed one or more depth values as height to a grid of plurality of vertices connected by a plurality of polygons.

\* \* \* \* \*